United States Patent
Tang et al.

(10) Patent No.: US 12,275,943 B2
(45) Date of Patent: Apr. 15, 2025

(54) **METHOD FOR INCREASING INTRACELLULAR HEME CONTENT OF *ESCHERICHIA COLI***

(71) Applicant: Jiangnan University, Wuxi (CN)

(72) Inventors: Lei Tang, Wuxi (CN); Mei Pan, Wuxi (CN); Shuangxin Liu, Wuxi (CN)

(73) Assignee: Jiangnan University, Wuxi (CN)

( * ) Notice: Subject to any disclaimer, the term of this patent is extended or adjusted under 35 U.S.C. 154(b) by 827 days.

(21) Appl. No.: 17/463,619

(22) Filed: Sep. 1, 2021

(65) Prior Publication Data

US 2021/0395755 A1 Dec. 23, 2021

Related U.S. Application Data

(63) Continuation of application No. PCT/CN2020/118317, filed on Sep. 28, 2020.

(30) Foreign Application Priority Data

Jul. 8, 2020 (CN) .......................... 202010651132.6

(51) Int. Cl.
| | | |
|---|---|---|
| *C12N 1/20* | (2006.01) | |
| *C12N 9/02* | (2006.01) | |
| *C12N 9/10* | (2006.01) | |
| *C12N 15/70* | (2006.01) | |

(52) U.S. Cl.
CPC .............. *C12N 15/70* (2013.01); *C12N 1/20* (2013.01); *C12N 9/0008* (2013.01); *C12N 9/1085* (2013.01); *C12Y 102/0107* (2013.01); *C12Y 205/01054* (2013.01)

(58) Field of Classification Search
CPC ....... C12P 17/10; C12N 15/74; C12N 9/1029; C12N 15/00; C12N 9/0004; C12N 15/11; C12N 9/0042; C12Y 106/02004; C12Y 114/11009; C12Y 114/13021; C12Y 401/01028
USPC ..................................................... 435/252.3
See application file for complete search history.

(56) References Cited

FOREIGN PATENT DOCUMENTS

| | | |
|---|---|---|
| CN | 106434509 A | 2/2017 |
| CN | 110591989 A | 12/2019 |
| WO | 2011133056 A1 | 10/2011 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Jeong et al. J. Mol. Biol. 2009, 394, pp. 644-652.*
Pan,Mei et. al. "Enhancing heme synthesis in *Escherichia coli* by regulating glutamic acid metabolism and over-expressing hemA" Microbilogy China, 2021-03-20, 48(3): 701-709.
Dassler T et. al. "Identification of a major facilitator protein from *Escherichia coli* involved in efflux of metabolites of the cysteine pathway" Molecular Microbiology Dec. 31, 2000, 36(5), 1101-1112.
Fu, Weiqi "Studies on 5-aminolevulinate production via recombinants optimization and process design" China Doctor's theses Full-text Database, Basic science, Dec. 15, 2010, pA006-53.

* cited by examiner

*Primary Examiner* — Robert B Mondesi
*Assistant Examiner* — Mohammad Y Meah
(74) *Attorney, Agent, or Firm* — IPRO, PLLC

(57) ABSTRACT

The disclosure discloses a method for increasing the intracellular heme content of *Escherichia coli* and belongs to the field of metabolic engineering. In the disclosure, in *E. coli*, the gene mscS encoding a small conductance mechanically sensitive ion channel protein is knocked out, the gene aroG encoding 3-deoxy-D-arabino-heptulosonate-7-phosphate synthase is knocked out, or the gene hemA encoding glutamyl-tRNA reductase is overexpressed. The constructed recombinant strain is cultured in an LB culture medium, and the heme content can reach 47.6 $\mu mol \cdot L^{-1}$, which is significantly higher than that of a control strain. The recombinant strain has the value of wide application.

7 Claims, 2 Drawing Sheets

Specification includes a Sequence Listing.

SEQUENCE LISTING

<160> NUMBER OF SEQ ID NOS: 6

<210> SEQ ID NO 1

<211> LENGTH: 861
<212> TYPE: DNA
<213> ORGANISM: Escherichia coli

<400> SEQUENCE: 1

```
atggaagatt tgaatgttgt cgatagcata acggcgcgg gaagctggct ggtagctaac      60
caggcgctgc tgctaagtta tgcagtaaac atcgtggcgg cactcgcgat catcatcgtt     120
ggtttgatta tcgcgcggat gatttccaac gcggtgaatc gcctgatgat ctcccgtaaa     180
atcgatgcca ctgttgctga ttttctttct gcattagtcc gttacggtat tatcgccttt    240
acgctaatcg ctgcactggg acgcgtgggt gtacaaaccg cgtcagtcat tgctgtactc    300
ggtgccgcag gcttagctgt tggtctggct ttgcaggggt cactgtctaa cctggccgct    360
ggcgtgttac ttgtcatgtt ccgcccgttc cgtgccggag aatatgttga cctgggcggc   420
gtagccggta ctgtgctgag tgtgcagatt ttctccacca ccatgcgtac tgcagacggt   480
aaaattatcg ttattccgaa cggtaaaatt attgccggaa atattattaa cttctcccgc   540
gagccagttc gccgtaacga atttattatt ggcgtggcgt atgattccga tatcgatcag   600
gttaagcaga tcctgaccaa tattatccag tctgaagatc gcattttgaa agatcgcgaa   660
atgactgtgc gcctgaacga acttggtgca tcgtcgatta atttcgtggt ccgcgtctgg   720
agcaacagcg gcgatctgca aaacgtgtac tgggatgtgc tggagcgtat taaacgtgaa   780
tttgatgccg ccggtatcag cttcccgtac ccgcaaatgg atgtgaactt taagcgggtg   840
aaagaagaca agctgcgta a                                               861
```

<210> SEQ ID NO 2
<211> LENGTH: 1053
<212> TYPE: DNA
<213> ORGANISM: Escherichia coli

<400> SEQUENCE: 2

```
atgaattatc agaacgacga tttacgcatc aaagaaatca agagttact tcctcctgtc      60
gcattgctgg aaaaattccc cgctactgaa atgccgcga atacggttgc ccatgcccga    120
aaagcgatcc ataagatcct gaaaggtaat gatgatcgcc tgttggttgt gattggccca    180
tgctcaattc atgatcctgt cgcggcaaaa gagtatgcca ctcgcttgct ggcgctgcgt    240
gaaagagctga agatgagct ggaaatcgta atgcgcgtct attttgaaaa gccgcgtacc    300
acggtgggct ggaaagggct gattaacgat ccgcatatgg ataatagctt ccagatcaac    360
gacggtctgc gtatagcccg taaattgctg cttgatatta cgacagcgg tctgccagcg    420
gcaggtgagt ttctcgatat gatcaccca caatatctcg ctgacctgat gagctggggc    480
gcaattggcg cacgtaccac cgaatcgcag gtgcaccgcg aactggcatc agggctttct   540
tgtccggtcg gcttcaaaaa tggcaccgac ggtacgatta agtggctat cgatgccatt    600
aatgccgccg gtcgccgcca ctgcttcctg tccgtaacga aatgggggca ttcggcgatt    660
gtgaatacca gcgtaacgg cgattgccat atcattctgc gcggcggtaa agagcctaac    720
tacagcgcga agcacgttgc tgaagtgaaa gaagggctga caaagcagg cctgccagca    780
caggtgatga tcgatttcag ccatgctaac tcgtccaaac aattcaaaaa gcagatggat    840
gtttgtgctg acgtttgcca gcagattgcc ggtggcgaaa aggccattat tggcgtgatg    900
gtggaaagcc atctggtgga aggcaatcag agcctcgaga gcggggagcc gctggcctac    960
ggtaagagca tcaccgatgc ctgcatcggc tgggaagata ccgatgctct gttacgtcaa   1020
ctggcgaatg cagtaaaagc gcgtcgcggg taa                                1053
```

<210> SEQ ID NO 3
<211> LENGTH: 1257
<212> TYPE: DNA
<213> ORGANISM: Escherichia coli

<400> SEQUENCE: 3

```
atgacccttt tagcactcgg tatcaaccat aaaacggcac ctgtatcgct gcgagaacgt    60
gtatcgtttt cgccggataa gctcgatcag gcgcttgaca gcctgcttgc gcagccgatg   120
gtgcagggcg gcgtggtgct gtcgacgtgc aaccgcacgg aactttatct tagcgttgaa   180
gagcaggata acctgcaaga ggcgttaatc cgctggcttt gcgattatca caatcttaat   240
gaagaagatc tgcgtaaaag cctctactgg catcaggata cgacgcggt tagccattta   300
atgcgtgttg ccagcggcct ggattcattg gttcttgggg agccgcagat cctcggtcag   360
gttaaaaaag cgtttgccga ttcgcaaaaa ggccatatga aggccagcga actggaacgc   420
atgttccaga atctttctc tgtagcgaaa cgcgttcgca ctgaaacaga tatcggtgcc   480
agcgctgtgt ctgtcgcttt tgcggcttgt acgctggcgc ggcagatctt tgaatcgctc   540
tctacggtca cagtgttgct ggtaggcgcg gcgaaaacca tcgagctggt agcgcgtcat   600
ctgcgcgaac ataaagtaca agatgatt atcgccaacc gcactcgcga acgtgcccaa   660
atactggcag atgaagttgg cgcggaagtg attgccctga gtgagatcga cgaacgtctg   720
cgcgaagccg atatcatcat cagttccacc gccagcccgt taccgattat cgggaaaggc   780
atggtggagc gcgcattaaa aagccgtcgc aaccaaccaa tgctgttggt ggatattgcc   840
gttccgcgcg atgttgagcc ggaagttggc aaactggcga atgcttatct ttatagcgtg   900
gacgatctgc aaagcatcat ttcgcacaac ctggcgcagc gtaaagccgc agcggttgag   960
gcggaaacta ttgtcgctca ggaaaccagc gaatttatgg cgtggctgcg agcacaaagc  1020
gccagcgaaa ccattcgcga gtatcgcagc caggcagagc aagttcgcga tgagttaacc  1080
gccaaagcgt tagcggccct tgagcagggc ggcgacgcgc aagccattat gcaggatctg  1140
gcatggaaac tgactaaccg cttgatccat gcgccaacga aatcacttca acaggccgcc  1200
cgtgacgggg ataacgaacg cctgaatatt ctgcgcgaca gcctcgggct ggagtag     1257
```

<210> SEQ ID NO 4
<211> LENGTH: 286
<212> TYPE: PRT
<213> ORGANISM: Escherichia coli

<400> SEQUENCE: 4

```
Met Glu Asp Leu Asn Val Val Asp Ser Ile Asn Gly Ala Gly Ser Trp
1               5                   10                  15

Leu Val Ala Asn Gln Ala Leu Leu Ser Tyr Ala Val Asn Ile Val
            20                  25                  30

Ala Ala Leu Ala Ile Ile Val Gly Leu Ile Ile Ala Arg Met Ile
        35                  40                  45

Ser Asn Ala Val Asn Arg Leu Met Ile Ser Arg Lys Ile Asp Ala Thr
    50                  55                  60

Val Ala Asp Phe Leu Ser Ala Leu Val Arg Tyr Gly Ile Ile Ala Phe
65                  70                  75                  80

Thr Leu Ile Ala Ala Leu Gly Arg Val Gly Val Gln Thr Ala Ser Val
                85                  90                  95

Ile Ala Val Leu Gly Ala Ala Gly Leu Ala Val Gly Leu Ala Leu Gln
                100                 105                 110
```

```
Gly Ser Leu Ser Asn Leu Ala Ala Gly Val Leu Val Met Phe Arg
            115                 120                 125
Pro Phe Arg Ala Gly Glu Tyr Val Asp Leu Gly Val Ala Gly Thr
130                 135                 140
Val Leu Ser Val Gln Ile Phe Ser Thr Thr Met Arg Thr Ala Asp Gly
145                 150                 155                 160
Lys Ile Ile Val Ile Pro Asn Gly Lys Ile Ala Gly Asn Ile Ile
                    165                 170                 175
Asn Phe Ser Arg Glu Pro Val Arg Arg Asn Glu Phe Ile Ile Gly Val
                180                 185                 190
Ala Tyr Asp Ser Asp Ile Asp Gln Val Lys Gln Ile Leu Thr Asn Ile
                195                 200                 205
Ile Gln Ser Glu Asp Arg Ile Leu Lys Asp Arg Glu Met Thr Val Arg
210                 215                 220
Leu Asn Glu Leu Gly Ala Ser Ser Ile Asn Phe Val Val Arg Val Trp
225                 230                 235                 240
Ser Asn Ser Gly Asp Leu Gln Asn Val Tyr Trp Asp Val Leu Glu Arg
                    245                 250                 255
Ile Lys Arg Glu Phe Asp Ala Ala Gly Ile Ser Phe Pro Tyr Pro Gln
                260                 265                 270
Met Asp Val Asn Phe Lys Arg Val Lys Glu Asp Lys Ala Ala
                275                 280                 285

<210> SEQ ID NO 5
<211> LENGTH: 350
<212> TYPE: PRT
<213> ORGANISM: Escherichia coli

<400> SEQUENCE: 5

Met Asn Tyr Gln Asn Asp Asp Leu Arg Ile Lys Glu Ile Lys Glu Leu
1               5                   10                  15
Leu Pro Pro Val Ala Leu Leu Glu Lys Phe Pro Ala Thr Glu Asn Ala
                20                  25                  30
Ala Asn Thr Val Ala His Ala Arg Lys Ala Ile His Lys Ile Leu Lys
            35                  40                  45
Gly Asn Asp Asp Arg Leu Leu Val Val Ile Gly Pro Cys Ser Ile His
        50                  55                  60
Asp Pro Val Ala Ala Lys Glu Tyr Ala Thr Arg Leu Leu Ala Leu Arg
65                  70                  75                  80
Glu Glu Leu Lys Asp Glu Leu Glu Ile Val Met Arg Val Tyr Phe Glu
                85                  90                  95
Lys Pro Arg Thr Thr Val Gly Trp Lys Gly Leu Ile Asn Asp Pro His
                100                 105                 110
Met Asp Asn Ser Phe Gln Ile Asn Asp Gly Leu Arg Ile Ala Arg Lys
            115                 120                 125
Leu Leu Leu Asp Ile Asn Asp Ser Gly Leu Pro Ala Ala Gly Glu Phe
        130                 135                 140
Leu Asp Met Ile Thr Pro Gln Tyr Leu Ala Asp Leu Met Ser Trp Gly
145                 150                 155                 160
Ala Ile Gly Ala Arg Thr Thr Glu Ser Gln Val His Arg Glu Leu Ala
                165                 170                 175
Ser Gly Leu Ser Cys Pro Val Gly Phe Lys Asn Gly Thr Asp Gly Thr
            180                 185                 190
```

```
Ile Lys Val Ala Ile Asp Ala Ile Asn Ala Ala Gly Ala Pro His Cys
            195                 200                 205

Phe Leu Ser Val Thr Lys Trp Gly His Ser Ala Ile Val Asn Thr Ser
            210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
            245                 250                 255

Gly Leu Pro Ala Gln Val Met Ile Asp Phe Ser His Ala Asn Ser Ser
            260                 265                 270

Lys Gln Phe Lys Gln Met Asp Val Cys Ala Asp Val Cys Gln Gln
            275                 280                 285

Ile Ala Gly Gly Glu Lys Ala Ile Ile Gly Val Met Val Glu Ser His
            290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
            325                 330                 335

Leu Leu Arg Gln Leu Ala Asn Ala Val Lys Ala Arg Arg Gly
            340                 345                 350

<210> SEQ ID NO 6
<211> LENGTH: 418
<212> TYPE: PRT
<213> ORGANISM: Escherichia coli

<400> SEQUENCE: 6

Met Thr Leu Leu Ala Leu Gly Ile Asn His Lys Thr Ala Pro Val Ser
1               5                   10                  15

Leu Arg Glu Arg Val Ser Phe Ser Pro Asp Lys Leu Asp Gln Ala Leu
            20                  25                  30

Asp Ser Leu Leu Ala Gln Pro Met Val Gln Gly Gly Val Val Leu Ser
            35                  40                  45

Thr Cys Asn Arg Thr Glu Leu Tyr Leu Ser Val Glu Glu Gln Asp Asn
    50                  55                  60

Leu Gln Glu Ala Leu Ile Arg Trp Leu Cys Asp Tyr His Asn Leu Asn
65                  70                  75                  80

Glu Glu Asp Leu Arg Lys Ser Leu Tyr Trp His Gln Asp Asn Asp Ala
            85                  90                  95

Val Ser His Leu Met Arg Val Ala Ser Gly Leu Asp Ser Leu Val Leu
            100                 105                 110

Gly Glu Pro Gln Ile Leu Gly Gln Val Lys Lys Ala Phe Ala Asp Ser
            115                 120                 125

Gln Lys Gly His Met Lys Ala Ser Glu Leu Glu Arg Met Phe Gln Lys
            130                 135                 140

Ser Phe Ser Val Ala Lys Arg Val Arg Thr Glu Thr Asp Ile Gly Ala
145                 150                 155                 160

Ser Ala Val Ser Val Ala Phe Ala Ala Cys Thr Leu Ala Arg Gln Ile
            165                 170                 175

Phe Glu Ser Leu Ser Thr Val Thr Val Leu Leu Val Gly Ala Gly Glu
            180                 185                 190

Thr Ile Glu Leu Val Ala Arg His Leu Arg Glu His Lys Val Gln Lys
            195                 200                 205
```

-continued

```
Met Ile Ile Ala Asn Arg Thr Arg Glu Arg Ala Gln Ile Leu Ala Asp
    210                 215                 220

Glu Val Gly Ala Glu Val Ile Ala Leu Ser Glu Ile Asp Glu Arg Leu
225                 230                 235                 240

Arg Glu Ala Asp Ile Ile Ile Ser Ser Thr Ala Ser Pro Leu Pro Ile
                245                 250                 255

Ile Gly Lys Gly Met Val Glu Arg Ala Leu Lys Ser Arg Arg Asn Gln
                260                 265                 270

Pro Met Leu Leu Val Asp Ile Ala Val Pro Arg Asp Val Glu Pro Glu
        275                 280                 285

Val Gly Lys Leu Ala Asn Ala Tyr Leu Tyr Ser Val Asp Asp Leu Gln
    290                 295                 300

Ser Ile Ile Ser His Asn Leu Ala Gln Arg Lys Ala Ala Ala Val Glu
305                 310                 315                 320

Ala Glu Thr Ile Val Ala Gln Glu Thr Ser Glu Phe Met Ala Trp Leu
                325                 330                 335

Arg Ala Gln Ser Ala Ser Glu Thr Ile Arg Glu Tyr Arg Ser Gln Ala
                340                 345                 350

Glu Gln Val Arg Asp Glu Leu Thr Ala Lys Ala Leu Ala Ala Leu Glu
            355                 360                 365

Gln Gly Gly Asp Ala Gln Ala Ile Met Gln Asp Leu Ala Trp Lys Leu
        370                 375                 380

Thr Asn Arg Leu Ile His Ala Pro Thr Lys Ser Leu Gln Gln Ala Ala
385                 390                 395                 400

Arg Asp Gly Asp Asn Glu Arg Leu Asn Ile Leu Arg Asp Ser Leu Gly
                405                 410                 415

Leu Glu
```

METHOD FOR INCREASING INTRACELLULAR HEME CONTENT OF ESCHERICHIA COLI

TECHNICAL FIELD

The disclosure relates to a method for increasing the intracellular heme content of *Escherichia coli*, specifically, using a technology combining gene knockout and overexpression, and belonging to the technical field of metabolic engineering.

BACKGROUND

Heme is an important type of iron-containing porphyrin compounds, which participates in electron transfer, decomposition of active oxygen, catalytic oxidation of substrates, control of gene expression, etc. In practical applications, heme can be used as a natural pigment for food additives, or as an iron supplement or anti-anemia drug in medical and health care, and can be used for *porphyria* treatment in the treatment of diseases. Heme is an important cofactor for cell respiration in most prokaryotic and eukaryotic organisms, and proteins with heme as a prosthetic group are essential for various biological processes. In the biosynthesis of recombinant enzymes with heme as a prosthetic group, insufficient heme is an important factor that leads to low enzyme activity. Therefore, an adequate supply of heme cofactors is of vital importance for the production of soluble and functional heme containing protein. In heterologous expression of recombinant proteins with heme as a prosthetic group, the increase in the intracellular heme content is beneficial to increase the ratio of active proteins.

SUMMARY

The disclosure discloses recombinant *E. coli*, with the gene mscS encoding a small conductance mechanically sensitive ion channel protein knocked out or silenced, the gene aroG encoding 3-deoxy-D-arabino-heptulosonate-7-phosphate synthase knocked out or silenced, the gene hemA encoding glutamyl-tRNA reductase overexpressed.

In one embodiment, the genes mscS and aroG are knocked out or silenced in *E. coli*.

In one embodiment, the gene mscS is knocked out or silenced and the gene hemA is overexpressed in *E. coli*.

In one embodiment, the genes mscS and aroG are knocked out or silenced in *E. coli*, and the gene hemA is overexpressed.

In one embodiment, the NCBI protein_id of the MscS protein is CAQ33235.1 (the amino acid sequence is as set forth in SEQ ID NO.4), the NCBI protein_id of the AroG protein is CAQ31213.1 (the amino acid sequence is as set forth in SEQ ID NO.5), and the NCBI protein_id of the glutamyl-tRNA reductase HemA is CAQ31712.1 (the amino acid sequence is as set forth in SEQ ID NO.6).

In one embodiment, the nucleotide sequence of the mscS gene is as set forth in SEQ ID NO.1; the nucleotide sequence of the aroG gene is as set forth in SEQ ID NO.2; and the nucleotide sequence of the hemA gene is as set forth in SEQ ID NO.3.

In one embodiment, *E. coli* BL21(DE3) is used as an original strain.

The disclosure discloses a method for producing heme, using the recombinant strain as a fermentation strain to produce heme.

In one embodiment, the recombinant strain is cultured overnight and then added to a culture system at an amount of 1 mL/100 mL.

In one embodiment, the culture system contains tryptone and yeast powder.

In one embodiment, the strain is cultured at 30-37° C. for 6-8 h.

The disclosure discloses application of the recombinant *E. coli* or the method in the production of heme.

The disclosure discloses a method for constructing the recombinant *E. coli*, and the method is to knock out the gene mscS or the gene aroG from the *E. coli* genome by the Red homologous recombination method.

In one embodiment, homologous arms of the gene as shown by the nucleotide sequence of SEQ ID NO.1 are designed, the homologous arms are 400-600 bp each upstream and downstream the gene, and then the gene mscS is knocked out from the *E. coli* genome by the Red homologous recombination method.

In one embodiment, homologous arms of the gene as shown by the nucleotide sequence of SEQ ID NO.2 are designed, the homologous arms are 40-60 bp each upstream and downstream the gene, and then the gene aroG is knocked out from the *E. coli* genome by the Red homologous recombination method.

In one embodiment, the gene hemA is ligated to a pET vector to construct an expression vector, and then the expression vector is transferred into a host cell.

Beneficial Effects

Compared with the original strain, the growth status of the genetically engineered strain does not significantly change, but the intracellular heme content is greatly increased. The recombinant strain pEA-MG, which genes aroG and mscS are knocked out and the gene hemA is overexpressed in *E. coli*, the heme content is 47.6 μmol·L$^{-1}$ after 7 hours of cultivation, which is significantly higher than that of the original strain and 23 times that of the original strain.

DETAILED DESCRIPTION

1. LB culture medium (g/L): Tryptone 10, yeast powder 5, NaCl 10, pH 7.0.

2. Determination of heme concentration:

The heme concentration is measured by a fluorescence method, specifically, an appropriate amount of bacterial cells cultured are taken, so that $OD_{600}$×the volume of bacterial liquid (mL)=8 (for example: if the $OD_{600}$ value of the bacterial cells is 0.4, then 20 mL of bacterial liquid is taken). The bacterial cells are centrifuged at 4° C. and 12000 r/min for 5 min to obtain bacterial cell precipitate. After washing with water, the bacterial cell precipitate is added to 1.5 mL amber centrifuge tubes. 500 μL of 20 mmol/L oxalic acid is added to each of the 1.5 mL centrifuge tubes, and the centrifuge tubes are allowed to stand overnight in a dark room at 4° C. for 16 h. 500 μL of 2 mol/L oxalic acid is added to each centrifuge tube. Half of the samples (for porphyrin concentration measurement) is taken to react at room temperature as the experimental control group, and the other half of the samples (for measurement of the total concentration of porphyrin and heme) is heated at 95° C. for 30 min. After natural cooling, the samples are centrifuged at 12000 r/min for 5 min. 200 μL of each sample is taken in a black 96-well plate for fluorescence detection (the excitation wavelength is 400 nm, and the emission wavelength is 620 nm). The difference between the two groups is the heme concentration to be measured.

3. Preparation of E. coli competent cells: Reference to the instruction of Takara Competent Cell Preparation Kit.

Example 1

According to SEQ ID NO.1, the upstream and downstream 500 bp homologous arms were designed respectively, and the mscS gene in E. coli BL21(DE3) was knocked out by the Red homologous recombination method (for specific steps, see Datsenko K A. One-step inactivation of chromosomal genes in E. coli K-12 using PCR products. Proceedings of the National Academy of Sciences of the United States of America, 2000, 97(12): 6640-6645). After validation by sequencing, a genetically engineered strain with the mscS gene knocked out was obtained and named WT-M.

The genetically engineered strain WT-M was inoculated into an LB culture medium and cultivated at 37° C. and 200 r/min overnight. On the next day, 500 μL of bacterial liquid of a certain concentration was transferred to 50 mL of LB culture medium and cultured at 37° C. and 200 r/min. The bacterial concentration was measured in real time and a growth curve was made, as shown in FIG. 2.

The strain WT was inoculated into an LB culture medium and cultivated at 37° C. and 200 r/min overnight. On the next day, a small amount of 500 μL of the same bacterial liquid was transferred to 50 mL of LB culture medium and cultured at 37° C. and 200 r/min. The bacterial concentration was measured in real time and a growth curve was made, as shown in FIG. 2.

Figure 1:
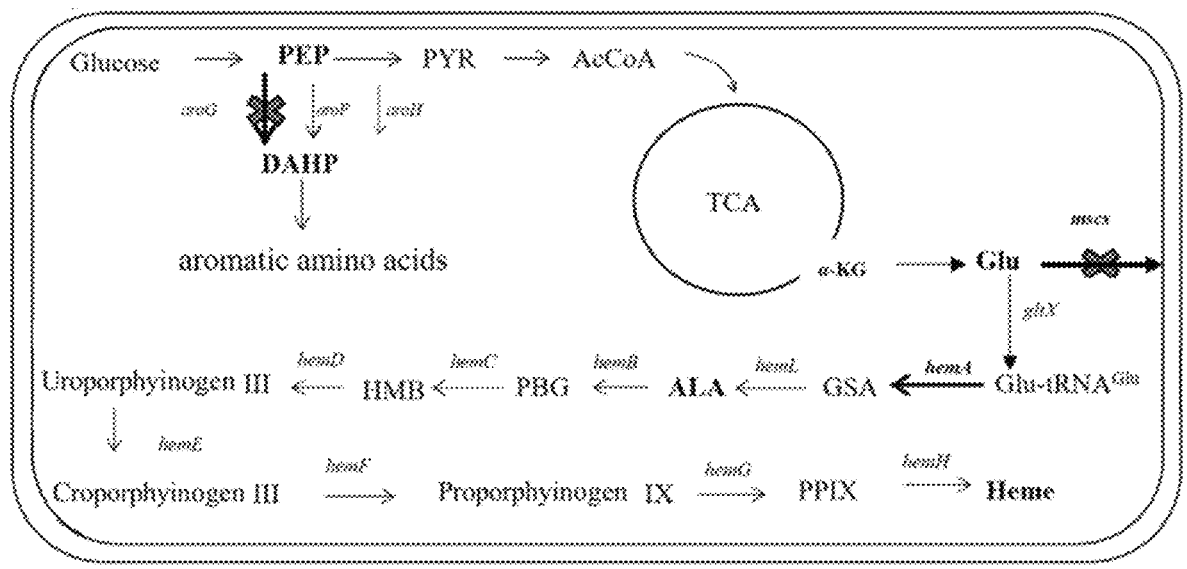
FIG. 1 is a diagram of the synthesis pathway of heme in *E. coli*; Notes: PEP, Phosphoenol-Pyruvate; PYR, Pyruvate; AcCoA, Acetyl-CoA; α-KG, α-Keto-Glutarate; Glu, Glutamate; GSA, Glutamate-1-semialdehyde; ALA, 5-aminolevulinic acid; PBG, Porphobilinogen; HMB, Hydroxymethylbilane; PPIX, Protoporphyin IX; DAH P, 3-deoxy-D-arabino-heptulosonate-7-phosphate; TCA, Citric acid cycle.
Figure 2:
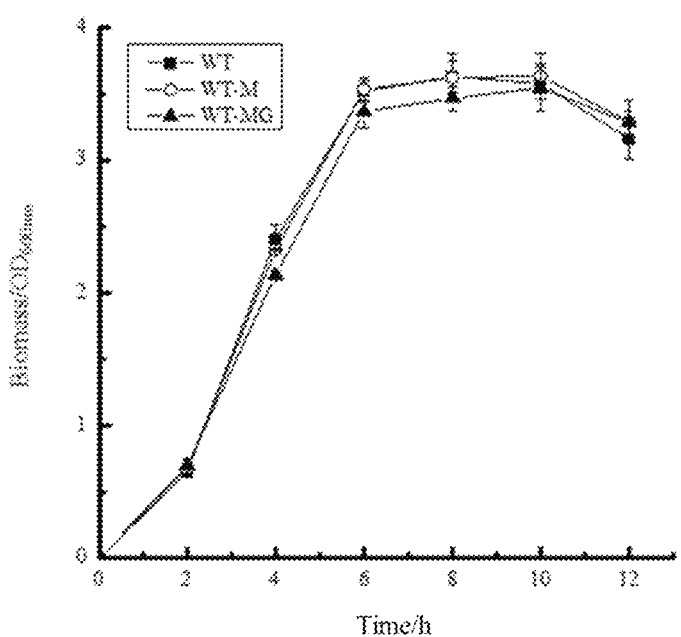
FIG. 2 shows the growth curve of each strain.
Figure 3:
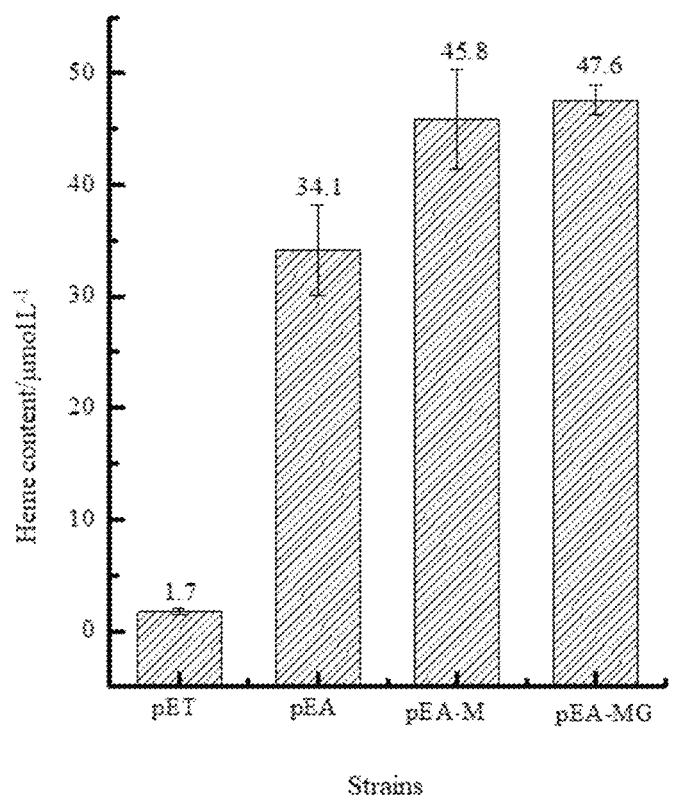
FIG. 3 is a graph of the heme content of each strain.

It can be seen from FIG. 2 that the genetically engineered strains WT-M and WT have no significant difference in growth.

After 7 h of culture, the heme content was measured, and the heme content of the WT and the WT-M was 2.11 μmol/L and 2.35 μmol/L respectively.

Example 2

According to SEQ ID NO.2, the upstream and downstream 50 bp homologous arms were designed respectively, and the aroG gene was knocked out by the Red homologous recombination method on the basis of WT-M. After validation by sequencing, a genetically engineered strain with the aroG gene knocked out was obtained and named WT-MG.

The genetically engineered strain WT-MG was inoculated into an LB culture medium and cultivated at 37° C. and 200 r/min overnight. On the next day, 500 μL of the bacterial liquid was transferred to 50 mL of LB culture medium and cultured at 37° C. and 200 r/min. The bacterial concentration was measured in real time, a growth curve was made, and as shown in FIG. 2, the genetically engineered strains WT-MG and WT have no significant difference in growth.

After 7 h of culture, the heme content of the WT-MG was measured and the heme content was 2.86 μmol/L.

Example 3

The glutamyl-tRNA reductase hemA gene (the nucleotide sequence of which is as set forth in SEQ ID NO.3) was ligated to a pET28a vector through Hind III and EcoR I to obtain the recombinant plasmid pET28a-hemA. Then the recombinant plasmid was transformed into JM109. The bacterial liquid was spread on an LB plate, and cultured at 37° C. until a single clone was grown. The single clone was picked and validated by sequencing, and the single clone which passed the validation was a positive transformant. The positive transformants were inoculated into an LB liquid culture medium and cultured for 8-12 h. The recombinant plasmid pET28a-hemA was extracted from the bacterial cell, and the recombinant plasmid was introduced into the strain WT-M obtained in Example 1 to obtain an engineered strain pEA-M. The heme concentration was measured by the fluorescence method. The result shows that the heme content of the pEA-M reaches 45.8 $\mu mol \cdot L^{-1}$.

The pET28a empty plasmid was transformed into BL21 to obtain an engineered strain pET. Using the above culture method, the engineered strain pET was cultured. The heme concentration was measured by the fluorescence method after the culture. The result shows that the heme content of the pET reaches 1.7 $\mu mol \cdot L^{-1}$.

Example 4

The specific implementation is the same as in Example 3. The difference is that the recombinant plasmid pET28a-hemA constructed in Example 3 was transformed into the strain WT-MG obtained in Example 2 to obtain an engineered strain pEA-MG. The heme concentration was measured by the fluorescence method. The result shows that the heme content of the pEA-MG reaches 47.6 $\mu mol \cdot L^{-1}$, which is 23 times that of the original strain WT.

Example 5

The specific implementation is the same as in Example 3. The difference is that the recombinant plasmid pET28a-hemA constructed in Example 3 was transformed into BL21 to obtain an engineered strain pEA. The heme concentration was measured by the fluorescence method. The result shows that the heme content of the pEA reaches 34.1 $\mu mol \cdot L^{-1}$.

Although the disclosure has been disclosed as above in preferred examples, it is not intended to limit the disclosure. Anyone familiar with this technology can make various changes and modifications without departing from the spirit and scope of the disclosure. Therefore, the protection scope of the disclosure should be defined by the claims.

What is claimed is:

1. A recombinant strain of *Escherichia coli*(*E. Coli*) comprising two or more of the following genetic mutations,
    (a) a knocked out or silenced mscS gene encoding a mechanically sensitive ion channel protein that is set forth in SEQ ID NO:1,
    (b) a knocked out or silenced aroG gene encoding a 3-deoxy-D-arabino-heptulosonate-7-phosphate synthase that is set forth in SEQ ID NO:2, and
    (c) an overexpressed hemA gene encoding a glutamyl-tRNA reductase that is set forth in SEQ ID NO:3.

2. The recombinant strain of claim 1, wherein the genes mscS and aroG are knocked out or silenced.

3. The recombinant strain of claim 1, wherein the gene mscS is knocked out or silenced and the gene hemA is overexpressed.

4. The recombinant strain of claim 1, wherein the genes mscS and aroG are knocked out or silenced, and the gene hemA is overexpressed.

5. The recombinant strain of claim 1, wherein the *E. coli* is *E. coli* strain BL21(DE3).

6. A method for producing heme, comprising;
    inoculating the recombinant strain of claim 1 into a culture medium,
    cultivating the strain overnight;
    transferring a portion of the strain containing culture medium to a new culture medium,
    and culturing the strain in the new culture medium, thereby producing the heme.

7. The method of claim 6, wherein the culture system comprises tryptone and yeast powder; and wherein the recombinant strain is cultured at 30° C. to 37° C. for 6 to 8 hours.

* * * * *